US005574162A

United States Patent [19]
Galbo et al.

[11] Patent Number: 5,574,162

[45] Date of Patent: *Nov. 12, 1996

[54] NON-MIGRATING 1-HYDROCARBYLOXY HINDERED AMINE DERIVATIVES AS POLYMER STABILIZERS

[75] Inventors: James P. Galbo, Hartsdale; Ramanathan Ravichandran, Nanuet, both of N.Y.; Peter J. Schirmann, Fairfield; Andrew Mar, Norwalk, both of Conn.

[73] Assignee: Ciba-Geigy Corporation, Tarrytown, N.Y.

[ * ] Notice: The term of this patent shall not extend beyond the expiration date of Pat. No. 5,004,770.

[21] Appl. No.: 456,212

[22] Filed: May 31, 1995

Related U.S. Application Data

[62] Division of Ser. No. 284,959, Aug. 2, 1994, Pat. No. 5,442,071, which is a division of Ser. No. 179,652, Jan. 7, 1994, Pat. No. 5,359,069, which is a division of Ser. No. 903,699, Jun. 24, 1992, Pat. No. 5,286,865, which is a division of Ser. No. 480,173, Feb. 14, 1990, Pat. No. 5,145,893, which is a continuation-in-part of Ser. No. 326,702, Mar. 21, 1989, abandoned.

[51] Int. Cl.$^6$ .................................. E07D 401/12
[52] U.S. Cl. ........................ 546/188; 546/14; 546/16; 546/186
[58] Field of Search ........................ 546/186, 216, 546/188, 223, 14, 16, 224

[56] References Cited

U.S. PATENT DOCUMENTS

| | | | |
|---|---|---|---|
| 4,145,512 | 3/1979 | Uhrhan et al. | 528/73 |
| 4,178,279 | 12/1979 | Uhrhan et al. | 8/178 |
| 4,344,876 | 8/1982 | Berner | 524/91 |
| 4,413,075 | 11/1983 | Di Battista | 524/102 |
| 4,426,471 | 1/1984 | Berner | 524/91 |
| 4,426,472 | 1/1984 | Berner | 524/99 |
| 4,605,743 | 8/1986 | Maly, Jr. et al. | 546/186 |
| 4,607,104 | 8/1986 | Malz, Jr. et al. | 546/102 |
| 4,691,015 | 9/1987 | Behrens et al. | 524/102 |
| 4,703,073 | 10/1987 | Winter et al. | 524/99 |
| 4,730,017 | 3/1988 | Avar | 524/103 |
| 4,831,134 | 5/1989 | Winter et al. | 524/102 |
| 4,876,300 | 10/1989 | Seltzer et al. | 524/102 |
| 4,921,962 | 5/1990 | Galbo et al. | 546/184 |
| 5,001,770 | 4/1991 | Cortolano | 524/99 |
| 5,006,577 | 4/1991 | Behrens et al. | 524/102 |
| 5,021,577 | 6/1991 | Galbo | 546/188 |
| 5,026,749 | 12/0000 | Cantatore et al. | 524/102 |
| 5,096,950 | 9/1992 | Galbo | 524/99 |
| 5,112,890 | 5/1992 | Behrens et al. | 524/95 |
| 5,204,473 | 4/1993 | Winter et al. | 546/188 |

FOREIGN PATENT DOCUMENTS

| | | |
|---|---|---|
| 1196444 | 11/1985 | Canada . |
| 0155912 | 9/1985 | European Pat. Off. . |
| 0303279 | 2/1989 | European Pat. Off. . |
| 0309402 | 3/1989 | European Pat. Off. . |
| 0323803 | 7/1989 | European Pat. Off. . |
| 0365481 | 4/1990 | European Pat. Off. . |
| 0138189 | 10/1981 | Japan . |

OTHER PUBLICATIONS

B. C. Miller et al. Radiat. Res. 88,369 (1981).
CA 106:1202635 (1987).
Hodgerman, "Studies on the reactions of UV Stabilizers", CA 99:1062289 (1983).
Keana, J. Ng. Chem. 36,209 (1971).
Callais et al. Proc. Water Borne High Solids Coating Symp. 16,486 (1989).
Shylapentakh Dev. in Polymer Stabilization 5, Applied Science publishers Ltd 1982, pp. 41–69.
Zhang et al. Inhibiting effect of radical polymerization of Vinyl Monomers Goadeng. Xuexlanee Huaxue Xuebao 7(9) 857–863 (1986).

Primary Examiner—Ceila Chang
Attorney, Agent, or Firm—Luther A. R. Hall

[57] ABSTRACT

1-Hydrocarbyloxy substituted hindered amine compounds which also contain a reactive functional group such as hydroxy, amino, oxirane or carboxyl can be chemically attached to selected polymer substrates by condensation reactions to give polymers containing a chemically-bonded, non-migrating stabilizer having excellent stabilization efficacy for protecting said polymer substrate from the adverse effects of actinic light.

6 Claims, No Drawings

NON-MIGRATING 1-HYDROCARBYLOXY HINDERED AMINE DERIVATIVES AS POLYMER STABILIZERS

This is a division of application Ser. No. 08/284,959, filed on Aug. 2, 1994, now U.S. Pat. No. 5,442,071, issued on Aug. 15, 1995; which is a division of application Ser. No. 08/179,652, filed on Jan. 7, 1994, now U.S. Pat. No. 5,359,069, issued on Oct. 25, 1994; which is a division of application Ser. No. 07/903,699, filed on Jun. 24, 1992, now U.S. Pat. No. 5,286,865, issued on Feb. 15, 1994; which is a division of application Ser. No. 07/480,173, filed on Feb. 14, 1990, now U.S. Pat. No. 5,145,893, issued on Sep. 8, 1992; which is a continuation-in-part of application Ser. No. 07/326,702, filed on Mar. 21, 1989, now abandoned.

BACKGROUND OF THE INVENTION

A compound to be an effective stabilizer in protecting a polymer substrate must remain in the substrate during processing and end-use conditions. One method of assuring this is to chemically bond the stabilizer to the polymer substrate backbone in some fashion. U.S. Pat. Nos. 4,145,512 and 4,178,279 describe polyurethane stabilized by incorporating 2,2,6,6-tetramethylpiperidine derivatives which contain amino, hydroxy or hydrazide moieties into the urethane prepolymer solution.

P. A. Callais et al, Proc. Water-Borne High Solids coating Symp., 16, 486 (1989) describe N-(2,2,6,6-tetra-methylpiperidin-4-yl)-N'-aminooxamide and N-(1-acetyl-2,2,6,6-tetramethylpiperidin-4-yl)-N'-aminooxamide reacted with acrylic polyols containing anhydride functionality. U.S. Pat. No. 4,730,017 teaches N-H, N-alkyl and N-acryl substituted 4-oxamido-2,2,6,6-tetramethylpiperidine derivatives bearing hydroxy groups.

None of the above references describe compounds having 1-hydrocarbyloxy groups present.

Specific 1-hydrocarbyloxy piperidine derivatives bearing a reactive functional groups have been described for applications other than polymer stabilization. N-Benzyloxy-4-hydroxy-2,2,6,6-tetramethylpiperidine has been detected during the photolysis of 4-hydroxy-1-oxyl-2,2,6,6-tetramethylpiperidine in toluene (J. F. W. Keana, J. Org. Chem, 36,209 (1971)). The N-(2-cyanopropan-2-yloxy)-piperidine derivative

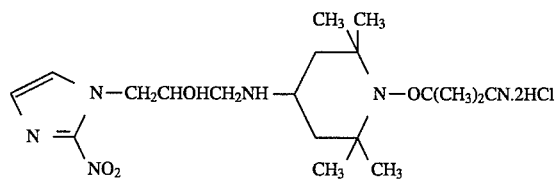

has been used in a study of nitroxyl radiosensitizers (B. C. Millar et al, Radiat Res, 88, (1981)).

The 1-hydrocarbyl(oxy) groups of the instant compounds contain only carbon and hydrogen. 1-Hydrocarbyloxy hindered amine derivatives are described in copending patent applications with Ser. Nos. 259,956; 099,418; 259,950; 259,958; 259,945; 259,944; 259,952; 259,949; 259,955 and 259,946.

DETAILED DESCRIPTION

The instant invention is directed to 1-hydrocarbyloxy substituted hindered amine compounds which also contains a reactive functional group, such as hydroxy, amino, oxirane, isocyanate, anhydride, oxazolidine, siloxane, allyl ether or carboxyl, elsewhere in the molecule allowing said compound to become chemically attached to selected polymer substrates by condensation reactions.

These 1-hydrocarboxyloxy substituted hindered amine compounds have the formula I, II, III, IV or V

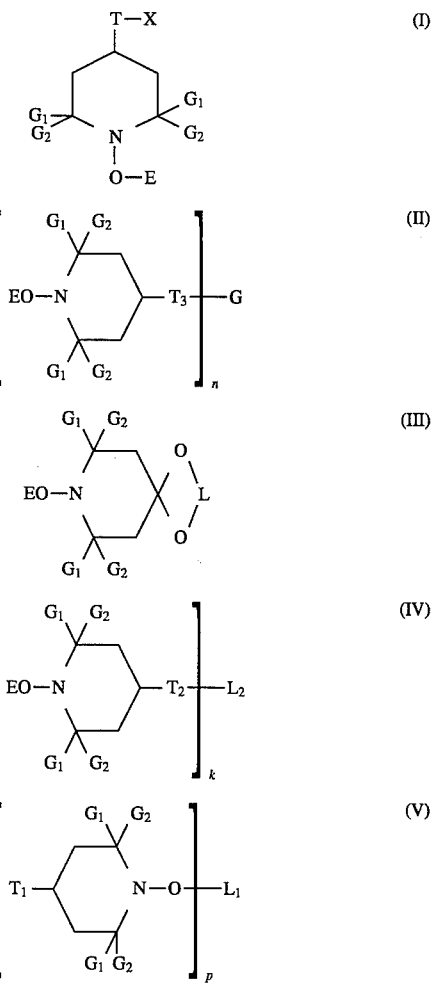

where
p is 2 to 10, $L_1$ is a p-valent radical of an alkane or alkene of 1 to 18 carbon atoms, a p-valent radical of a cycloalkane or cycloalkene of 5 to 12 carbon atoms, a p-valent radical of a saturated or unsaturated bicyclic or tricyclic hydrocarbon of 7 to 12 carbon atoms or a p-valent radical of an aryl, alkyl substituted aryl or aralkyl hydrocarbon of 6 to 15 carbon atoms, with the proviso that the N-O groups are not necessarily attached to the same carbon atom in $L_1$, $T_1$ is —OH, —$NHR_2$, —NCO, —O—glycidyl or $Si(OR_1)_3$, $G_1$ and $G_2$ are independently alkyl of 1 to 4 carbon atoms, or $G_1$ and $G_2$ together are pentamethylene, T is a direct bond, —$CO(CH_2)m$—, —$COO(CH_2)_m$—, —$NR_1CO(CH_2)_m$—, —$(OCH_2CH_2)_y$—, —$[OCH_2CH(CH_3)]_y$—, alkylene of 1 to 6 carbon atoms, said alkylene interrupted by one or more oxygen atoms, —NHCO—, —$NR_1COCONR_1$—, —OCO—, —OCO$(CH_2)_m$—, —$NR_1COCONR_1CH_2CH_2$— or —$NR_1COCONR_1CH_2CH(CH_3)$— where $R_1$ is hydrogen or alkyl of 1 to 12 carbon atoms, m is 2 or 3, y is 1 to 10, and the hetero oxygen or nitrogren atom is attached to the piperidyl ring, X is —OH, —NHR$_2$, —COOH, —NCO, —O—glycidyl or Si(OR$_1$)$_3$ where R$_2$ is hydrogen, alkyl of 1 to 12 carbon atoms, or

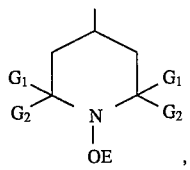

with the proviso that, when X is —NHR$_2$, T is not a direct bond,

E is alkyl of 1 to 18 carbon atoms, cycloalkyl of 5 to 12 carbon atoms, alkenyl of 2 to 18 carbon atoms, cycloalkenyl of 5 to 12 carbon atoms, aralkyl of 7 to 15 carbon atoms, a radical of a saturated or unsaturated bicyclic or tricyclic hydrocarbon of 7 to 12 carbon atoms or aryl of 6 to 10 carbon atoms or said aryl substituted by alkyl, L is —CH$_2$  or
—CHCH$_2$CH$_2$OH

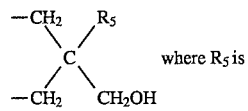  where R$_5$ is methyl, ethyl or —CH$_2$OH;

with the proviso that E is not benzyl, when T is a direct bond and X is —OH, n is 1 to 4,

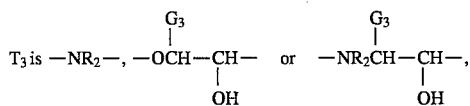

G$_3$ is hydrogen or G$_4$,

G$_4$ is alkyl having 1 to 36 carbon atoms, cycloalkyl having 5 to 12 carbon atoms, phenyl or naphthyl which is unsubstituted or substituted by alkyl of 1 to 36 carbon atoms or aralkyl having 7 to 9 carbon atoms which is unsubstituted or substituted by alkyl having 1 to 36 carbon atoms, when n is 1, G is G$_4$ or

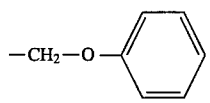

or G and G$_3$ together with the carbon atoms to which they are attached form a ring containing 5 to 12 carbon atoms;

when n is 2, G is alkylene having 2 to 12 carbon atoms or

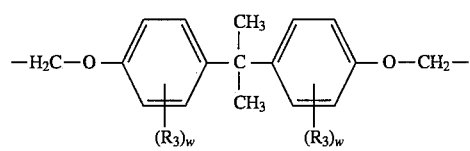

wherein w is 1 or 2 and R$_3$ is hydrogen, alkyl or alkoxy each having 1 to 4 carbon atoms, hydroxyl, halogen, cyano or nitro or

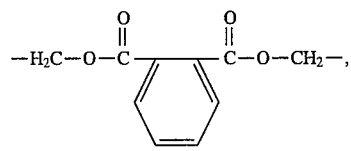

or G is —CHOH— or —CH$_2$CH(CH$_2$OH)—,
or G is —T—CO—O—CO—T—,
when n is 3, G is

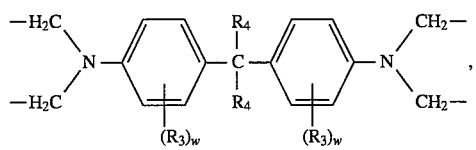

and, when n is 4, G is

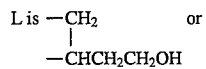

wherein R$_4$ is hydrogen or methyl and R$_3$ and w are as previously defined, k is 1 to 100, L$_2$ is an oligomeric or polymeric backbone derived from poly(vinyl alcohol), poly(acrylic acid), poly(methacrylic acid) or poly(maleic acid) having at least one free —OH or —COOH group present; or L$_2$ is a residue of a monosaccharide, a disaccharide or a polysaccharide having one or more free —OH group present; or L$_2$ is a residue of an oligomeric or polymeric structure derived from an ethylenically unsaturated material which has then been epoxidized, having one or more free —OH group present, and T$_2$ is —O—, —NR$_2$—, —OCH$_2$CHOHCH$_2$—, —NR$_2$CHOHCH$_2$—, —OCONH—R$_6$—NHCO— or —NR$_2$COONH—R$_6$—NHCO—, where R$_6$ is the aliphatic, cycloaliphatic or aromatic divalent radical obtained by removing two —NCO moieties from an aliphatic, cycloaliphatic or aromatic diisocyanate of 4 to 15 carbon atoms.

Preferably G$_1$ and G$_2$ are each methyl.

Preferably E is alkyl of 1 to 18 carbon atoms, alkenyl of 2 to 3 carbon atoms, propargyl or cyclohexyl.

Most preferably E is methyl, heptyl, octyl, nonyl or cyclohexyl.

Preferably L$_1$ is an n-valent radical of n-octane, n-heptane or cyclohexane.

Preferably T is a direct bond.

Preferably T$_1$ is —OH or —NH$_2$.

Preferably X is —OH.

Preferably —T$_3$—G—T$_3$— is —OCH$_2$CHOHCH$_2$O—.

When E is alkyl, E is, for example, methyl, ethyl, butyl, amyl, heptyl, octyl, nonyl, dodecyl tetradecyl, octadecyl, eicosyl, tricosyl or tricontyl.

When E is alkenyl, E is, for example, vinyl, allyl, octenyl or oleyl.

When E is alkynyl, E is, for example, propargyl.

When E is cycloalkyl, E is, for example, cyclopentyl, cyclohexyl, cyclooctyl or cyclododecyl.

Preferably the instant compound has formula I.

Suitable alkyl radicals for $G_3$ and $G_4$ are, for example, methyl, ethyl, propyl, butyl, pnetyl, hexyl, octyl, decyl, tetradecyl, hexadecyl, eicosyl, docosyl, pentacosyl, heptacosyl, triacontyl, dotriacontyl, tetratriacontyl and hexatriacontyl as well as branched isomers thereof.

As cycloalkyl, $G_3$ and $G_4$ are, for example, cyclopentyl, cyclohexyl, cycloheptyl, cyclooctyl, cyclodecyl and cyclododecyl.

$G_3$ and $G_4$ are aralkyl having 7 to 9 carbon atoms include benzyl, phenylethyl or phenylpropyl.

when n denotes 1 and G and $G_3$ together with the carbon atoms to which they are attached form a ring containing 5 to 12 carbon atoms, the ring is a saturated carbocyclic ring and thus includes cyclopentyl, cyclohexyl, cyclooctyl, cyclononyl or cyclododecyl.

When n is 2, G as alkylene having 2 to 12 carbon atoms includes ethylene, propylene, butylene, hexylene, octylene, nonylene, decylene, dodecylene or branched isomers thereof.

when n is 3, and G is an ether radical of the formula

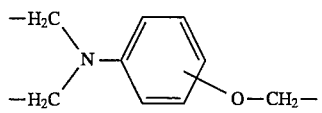

the —O—$CH_2$— group preferably occupies the para-position to the —N($CH_2$—)$_2$-substituent on the phenyl ring.

When n is 4 and G represents a radical of the formula

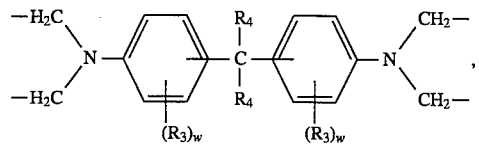

the —C($R_4$)$_2$—moiety is preferably attached in para-position to each —N($CH_2$—)$_2$ substituent on the phenyl ring.

In the preferred compounds, $G_4$ is alkyl having 1 to 18 carbon atoms, cycloalkyl having 5 to 8 carbon atoms, phenyl, benzyl or phenylethyl, $G_3$ is hydrogen, n is 1 to 4, and, when n is 1, G is $G_4$ or —$CH_2$—O—$C_6H_5$, when n is 2, G is alkylene having 2 to 5 carbon atoms

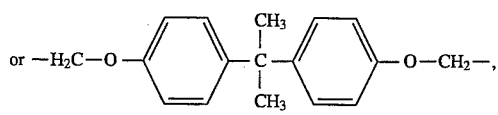

when n is 3, G is

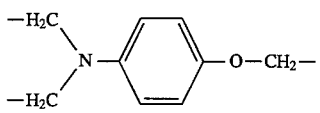

and when n is 4, G is

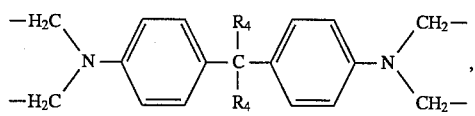

where $R_4$ is as defined.

More preferably, $G_4$ is alkyl having 3 to 6 or 8 to 18 carbon atoms, cyclohexyl, cyclooctyl, phenyl or benzyl and n is 1 to 2, and, when n is 1, G is $G_4$ or —$CH_2$—O—$C_6H_5$ and when n is 2, G is alkylene having 2 or 3 carbon atoms or

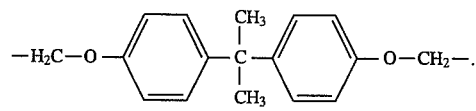

The instant compounds of formula I having the reactive functional group X (or in the case of formula II or III where said group is —OH) can react with polymer intermediates, with prepolymers or with polymers having a number of functional terminal or pendant moieties thereon to become chemically bonded by condensation reactions to the polymer through ester, amide, urethane, ether or other chemical linkages. This results in a polymer chain having a multiplicity of 1-hydrocarbyloxy-hindered amine moieties firmly attached thereto said moieties now being anchored firmly to the polymer preventing the untoward loss of stabilizer by volatilization or sublimation and preventing migration of the stabilizer from its proper site in the polymer to be stabilized. Superior stabilization performance is the result.

The instant compounds react by condensation reactions with polymer intermediates, prepolymers or polymers having pendant or terminal functional moieties selected from the group consisting of anhydrides, epoxides, carboxylic acids, siloxanes, hydroxyl groups, amines, isocyanates and alkoxymethylmelamine.

The instant compounds are prepared from intermediats which are largely items of commerce.

The instant oligomeric compounds can be prepared by modifications of the methods for preparing monomeric N-hydrocarbyloxy compounds.

One convenient method involves the reaction of a (N-oxyl) or (N-hydroxy) hindered amine with a polyhaloalkane.

Most conveniently the instant polysubstituted compounds are prepared by coupling a (N-oxyl) hindered amine with a hydrocarbon n-valent radical generated from the decomposition of a peroxide or hydroperoxide in the presence of a hydrocarbon having abstractable hydrogen atoms.

The ratio of (N-oxyl)hindered amine to hydrocarbon can be adjusted to favor the formation of toohomeric N-hydrocarbyloxy compounds or the formation of the instant polysubstituted N-hydrocarbyloxy compounds, but mixtures of monomeric and polysubstituted N-hydrocarbyloxy compounds are nearly always obtained. These mixtures can be easily separated into toohomeric and polysubstituted N-hydrocarbyloxy compounds by column chromatography.

When a (N-oxyl) or (N-hydroxy) hindered amine reacted with a polyhaloalkane, instant compounds of discrete structures are obtained.

Although the instant application emphasizes the 2,2,6,6-tetraalkylpiperidine structure, it is to be noted that the invention also relates to compounds wherein the following tetraalkyl substituted piperazine or piperazinone moieties are substituted for the above-noted tetraalkylpiperidine moiety:

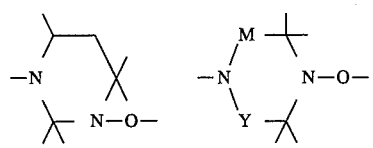

wherein M and Y are independently methylene or carbonyl, preferably M being methylene and Y being carbonyl. It is understood that the identified substituents applicable to such compounds are those which are appropriate for substitution on the ring nitrogen atoms.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include

1. Polymers of monoolefins and dioleftns, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate] mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as blockcopolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester res;Ins which are derived from copolyesters of saturated and unsaturated dicarboxylic acids with polyhydric alcohols and vinyl compounds as crosslinking agents, and also halogen-containing modifications thereof of low flammability.

23. Thermoserring acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose buryrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsionis of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE 4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants
1.1. Alkylated monophenols, for example,
2,6-di-tert-butyl-4-methylphenol
2-tert.butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(-methylcyclohexyl)-4,6-dimethylphenol
2,6-di-octadecyl-4-methylphenol
2,4,6-tri-cyclohexylphenol
2,6-di-tert-butyl-4-methoxymethylphenol
1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol
1.3. Hydroxylated thiodiphenyl ethers, for example
2,2'-thio-bis-(6-tert-butyl-4-methylphenol )
2,2'-thio-bis-(4-octylphenol)
4,4'-thio-bis-(6-tert-butyl-3-methylphenol)
4,4'-thio-bis-(6-tert-butyl-2-methylphenol)
1.4. Alkyl idene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α(-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α(-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalate.
1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl)sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl)isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt
1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate
1.7. Esters of β-(3,5-di-tert-butyl-4-hydroxyphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxycinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert .butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5tetramethylpiperazinone).

2.7. Oxalic acid diamides, for example, 4,4'-di-octyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-as well as of o-and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis [2-hydroxy-4-(2-hydroxyethoxy)phenyl]-6-(4-chlorophenyl)-s-triazine; 2,4-bis [2-hydroxy-4-(2-hydroxyethoxy)phenyl]-6-phenyl-s-triazine; 2,4-bis [2-hydroxy-4-(2-hydroxyethoxy)phenyl]-6-(2,4-dimethylphenyl)-s-triazine; 2,4-bis [2-hydroxy-4-(2-hydroxyethoxy)phenyl]-6-(4-bromophenyl)-s-triazine; 2,4-bis [2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazinc, 3-salicyloylamino-1, 2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl )pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithio-carbamate, dioctadecyl disulftde, pentaerythritol tetrakis-(β-dodecylmercapto)-propionate.

6. Hydroxylamines, for example, N,N-dibenzylhydroxylamine, N,N-d iethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Polyamide stabilizers, for example copper salts in combination with iodides and/or phosphorus compounds and salts of divalent manganese.

8. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and palmitate, antimony pyrocatecholate or zinc pyrocatecholate.

9. Nucleating agents, for example, 4-tert-butyl-benzoic acid, adipic acid, diphenylacetic acid.

10. Fillers and reinfoircing agents, for example, calcium carbonate, silicates, glass fibers, asbestos, talc, kaolin, mica, barium sulfate, metal oxides and hydroxides, carbon black, graphite.

11. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

Of particular interest is the utilization of the instant derivatives in a variety of coating systems including ambient cured and acid catalyzed coating systems. In particular, the physical integrity of the coatings is maintained to a higher degree with significant reduction in loss of gloss and yellowing. Key improvements include the substantial absence of the cure retardation encountered with N-alkyl hindered amine light stabilizers; the substantial absence of flocculation and dispersion destabilization seen when N-alkyl hindered amines are utilized in certain pigmented coating systems and the absence of adhesion loss between the coating and polycarbonate substrate. Accordingly, the present invention also relates to the use of the instant compounds, optionally together with further stabilizers, for stabilizing ambient cured coatings based on alkyd resins; thermoplastic acrylic resins; acrylic alkyds; acrylic alkyd or polyester resins optionally modified with silicon, isocyanates, isocyanurates, ketimines or oxazolidines; and epoxy resins crosslinked with carboxylic acids, anhydrides, polyamines or mercaptans; and acrylic and polyester resin systems modified with reactive groups in the backbone thereof and crosslinked with epoxides; against the degradative effects of light, moisture and oxygen.

Furthermore, in their industrial uses, enamels with high solids content based on crosslinkable acrylic, polyester, urethane or alkyd resins are cured with an additional acid catalyst. Light stabilizers containing a basic nitrogen group are generally less than satisfactory in this application. Formation of a salt between the acid catalyst and the light stabilizer leads to incompatibility or insolubility and precipitation of the salt and to a reduced level of cure and to reduced light protective action and poor resistance to moisture.

These acid catalyzed stoving lacquers are based on hot crosslinkable acrylic, polyester, polyurethane, polyamide or alkyd resins. The acrylic resin lacquers, which can be stabilized against light, moisture and oxygen in accordance with the invention, are the conventional acrylic resin storing lacquers or thermosetting resins including acrylic/melamine systems which are described, for example, in H. Kittel's "Lehrbuch der Lacke und Beschichtungen", Vol 1 Par 2, on pages 735 and 742 (Berlin 1972), "Lackkunstharze" (1977), by H. Wagner and H. F. Sarx, on pages 229–238, and. in S. Paul's "Surface Coatings: Science and Technology" (1985).

The polyester lacquers, which can be stabilized against the action of light and moisture, are the conventional storing lacquers described e.g. in H. Wagner and H. F. Sarx, op. cit., on pages 86–99.

The alkyd resin lacquers which can be stabilized against the action of light and moisture in accordance with the invention, are the conventional storing lacquers which are used in particular for coating automobiles (automobile finishing lacquers), for example lacquers based on alkyd/melamine resins and alkyd/acrylic/melamine resins (see H. Wagner and H. F. Sarx, op. cit., pages 99–123). Other crosslinking agents include glycoluril resins, blocked isocyanates or epoxy resins.

The acid catalyzed stoving lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the instant substituted hindered amines are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines, and the like.

Correspondingly, the epoxide may be utilized as the crosslinking agent for various acrylic or polyester resin systems that have been modified by the presence of reactive groups on the backbone structure.

To attain maximum light stability in such coatings, the concurrent use of other conventional light stabilizers can be advantageous. Examples are the aforementioned UV absorbers of the benzophenone, benzotriazole, acrylic acid derivative, or oxanilide type, or aryl-s-triazines or metal-containing light stabilizers, for example organic nickel compounds. In two-coat systems, these additional light stabilizers can be added to the clear coat and/or the pigmented base coat.

If such combinations are employed, the sum of all light stabilizers is 0.2 to 20% by weight, preferably 0.5 to 5% by weight, based on the film-forming resin.

Examples of difference classes of UV absorbers which may be used in the instant compositions in conjunction with the aforementioned piperidine compounds are referenced in a paper by H. J. Heller in European Polymer Journal Supplement, 1969, pp 105–132. These classes include the phenyl salicylates, the o-hydroxybenzophenones, the hydroxyxanthones, the benzoxazoles, the benzimidazoles, the oxadiazoles, the triazoles, the pyrimidines, the chinazolines, the s-triazines, the hydroxyphenyl-benzotriazoles, the alpha-cyanoacrylates and the benzoates.

Types of UV absorbers of especial importance are:

(a) 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy-, and 3',5'-di-tert-amyl derivatives.

(b) 2-Hydroxy-benzophenones, for example, the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'-dimethoxy derivatives.

(c) Acrylates, for example, alpha-cyano-β,β-diphenylacrylic acid ethyl ester or isoctyl ester, alpha-carbo-methoxy-cinnamic acid methyl ester, alpha-cyano-β-methyl-β-p-methoxy-cinnamic acid methyl ester or butyl ester, alpha-carbomethoxy-p-methoxy-cinnamic acid methyl ester, N-(β-carbomethoxy-β-cyanovinyl)-2-methyl-indoline.

(d) Nickel compounds, for example, nickel complexes of 2,2'-thiobis-[4-(1,1,3,3-tetramethylbutyl)-phenol], such as the 1:1 or 1:2 complex, optionally with additional ligands such as n-butylamine, triethanolamine or N-cyclo-hexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketonoxime, nickel complexes of 1-phenyl-4-lauroyl-5-hydroxy-pyrazol, optionally with additional ligands.

(e) Oxalic acid diamides, for example, 4,4'-di-octyl-oxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethylaminopropyl)-oxalamide, 2-ethoxy-5-tert-butyl-2'-ethyl-oxanilide and its mixture with 2-ethoxy-2'-ethyl-5,4'-di-tert-butyl-oxanilide and its mixtures of ortho- and para-methoxy- as well as of o- and p-ethoxy-disubstituted oxanilides.

(f) Hydroxyphenyl-s-triazines such as 2,6-bis(2,4-di-methylphenyl)-4-(2-hydroxy-4-octyloxyphenyl)-s-triazine or the corresponding 4-(2,4-dihydroxyphenyl) derivative.

Of particular value in the instant compositions are the benzotriazoles of high molecular weight and low volatility such as 2-[2-hydroxy-3,5-di(alpha,alpha-di-methylbenzyl)-phenyl]-2H-benzotriazole, 2-(2-hydroxy-3,5-di-tert-octylphenyl)-2H-benzotriazole, 2-(2-hydroxy-3-alpha,alpha-dimethylbenzyl-5-tert-octyl-phenyl)-2H-benzotriazole, 2-(2-hydroxy-3-tert-octyl-5-alpha,alpha-dimethyl-benzylphenyl)-2H-benzotriazole, 2-(2-hydroxy-3,5-di-tert-amylphenyl)-2H-benzotriazole, 2-[2 -hydroxy-3-tert-butyl-5-(2-(omega-hydroxy-octa-(ethyleneoxy)carbonyl)-ethylphenyl]-2H-benzotriazole, dodecylated 2-(2-hydroxy-5-methylphenyl)-2H-benzotriazole, 2-[2-hydroxy-3-tert.butyl-5-(2-octyloxycarbonyl) ethylphenyl]-2H-benzotriazole and the 5-chloro compounds corresponding to each of the above named benzotriazoles.

Most preferably the benzotriazoles useful in the instant compositions are 2-[2-hydroxy-3,5-di(alpha,alpha-dimethyl-benzyl)phenyl]-2H-benzotriazole, dodecylated 2-(2-hydroxy-5-methylphenyl)-2H-benzotriazole, 2-[2-hydroxy-3-tert-butyl- 5-(2-(omega-hydroxy-octa-(ethyleneoxy)carbonyl)-ethylphenyl]-2H-benzotriazole, 2-[2-hydroxy-3-tert-butyl-5-(2-octyloxycarbonyl)ethylphenyl]-2H-benzotriazole and 5-chloro-2-[2-hydroxy-3-tert.butyl-5-(2-octyloxycarbonyl) ethylphenyl]-2H-benzotriazole.

It is also contemplated that the instant compounds will be particularly effective as stabilizers for polyolefin fibers, especially polypropylene fibers, when used in conjunction with other stabilizers selected from the group consisting of the phenolic antioxidants, hindered amine light stabilizers, organic phosphorus compounds, ultraviolet absorbers and mixtures thereof.

A preferred embodiment of the instant invention pertains to stabilized compositions comprising (a) an acid catalyzed thermoset coating or enamel based on hot crosslinkable acrylic, polyester or alkyd resins, (b) a NOE-substituted 2,2,6,6-tetraalkylpiperidine compound, and (c) a UV absorber selected from the group consisting of the benzophenones, benzotriazoles, acrylic acid derivatives, organic nickel compounds, aryl-s-triazines and oxanilides.

Further ingredients which the enamels or coatings can contain are antioxidants, for example those of the sterically hindered phenol derivatives, phosphorus compounds, such as phosphites, phosphines or phosphonites, plasticizers, levelling assistants, hardening catalysts, thickeners, dispersants or adhesion promoters.

A further preferred embodiment of the instant invention is a stabilized composition containing components (a), (b) and (c) described above which additionally contains as component (d) a phosphite or phosphonite.

The amount of phosphite or phosphonite (d) which is used in the instant compositions is from 0.05 to 2% by weight, preferably from 0.1 to 1% by weight, based on the film forming resin. In two-coat systems, these stabilizers may be added to the clear coat and/or base coat.

Typical phosphite and phosphonites include triphenyl phosphite, diphenylalkyl phosphites, phenyldialkyl phosphites, tri-(nonylphenyl)phosphite, trilauryl phosphite trioctadecyl phosphite, di-stearyl-pentaerythritol diphosphite, tris-(2,4-di-tert.butylphenyl) phosphite, di-isodecylpentaerythritol diphosphite, di-(2,4-di-tert.butylphenyl) pentaerythritol diphosphite, tristearyl-sorbitol triphosphite, tetrakis-(2,4-di-tert.butylphenyl )-4,4'di-phenylylenediphosphonite.

The acid catalyzed thermoset enamels must be stabilized in order to function acceptably in end-use applications. The stabilizers used are hindered amines, preferably those substituted on the N-atom by an inert blocking group in order to prevent precipitation of the basic amine stabilized with the acid catalyst with a concomitant retardation in cure, optionally in combination with UV absorbers, such as the benzotrtazoles, benzophenones, substituted s-triazines, phenyl benzoates or oxanilides.

The stabilizers are needed to impart greater retention of durability to the cured enamels (as measured by 20° gloss, distinction of image, cracking or chalking); the stabilizers must not retard cure (normal bake for auto finishes at 121° C. and low bake repair at 82° C. (as measured by hardness, adhesion, solvent resistance and humidity resistance), the enamel should not yellow on curing and further color change on exposure to light should be minimized; the stabilizers should be soluble tn the organic solvents normally used in coating applications such as methyl amyl ketone, xylene, n-hexyl acetate, alcohol and the like.

The instant hindered amine light stabilizers substituted on the N-atom by an O-substituted moiety fulfill each of these requirements and provide alone or in combination with a UV-absorber outstanding light stabiliza.tion protection to the cured acid catalyzed thermoset enamels.

Still another preferred combination of the instant stabilizers is with a hydroxylamine in order to protect polypropylene fibers from gas fading.

The following examples are presented for the purpose of illustration only and are not to be construed to limit the nature or scope of the instant invention in any manner whatsoever.

Example 1A

4-Benzoyloxy-1-methoxy-2,2,6,6-tetramethylpiperidine

A solution of 20.0 grams (72 mmol) of 4-benzoyloxy-1-oxyl-2,2,6,6-tetramethylpiperidine, 10.5 grams (72 mmol) of di-tert-butyl peroxide, and 30 ml of chlorobenzene is heated for six hours in a Fischer-Porter pressure bottle (nitrogen atmosphere, bath temperature 145°–150° C.). The crude reaction product is purified by flash chromatography (silica gel; 50:1 heptane:ethyl acetate) and then recrystallized from methanol to afford 10.8 grams (51% yield) of the title compound, a white solid melting at 67°–68° C.
Analysis:
Calcd for $C_{17}H_{25}NO_3$: C, 70.1; H, 8.7; N, 4.8.
Found: C, 70.0; H, 8.8; N, 4.8.

Example 1B

4-Hydroxy-1-methoxy-2,2,6,6-tetramethylpiperidine

The ester obtained in Example 1A is hydrolyzed using potassium hydroxide aqueous methanol to yield the title compound as a white solid melting at 92°–93° C.
Analysis:
Calcd for $C_{10}H_{21}NO_2$: C, 64.1; H, 11.3; N, 7.5.
Found: C, 64.1; H, 11.6; N, 7.4.

Example 2A

4-Benzoyloxy-1-cyclohexyloxy-2,2,6,6-tetramethylpiperidine

A mixture of 10.5 grams (40.2 mmol) of 4-benzoyloxy-2,2,6,6-tetramethylpiperidine, 16.1 grams (160.8 mmol) of 90% tert-butyl hydroperoxide, 600 mg of molybdenum trioxide and 60 ml of cyclohexane is placed in a Fischer-Porter pressure bottle (nitrogen atmosphere) in an oil bath. The bath temperature is gradually increased to 135° C. over a 2.25 hour period and then maintained at 135° C. for another 2.25 hours till the red color of the N-oxyl intermediate is discharged. Solids are removed by filtration. The cyclohexane solution is washed twice with water, then with saturated sodium chloride solution and dried over anhydrous magnesium sulfate, and finally concentrated under reduced pressure to obtain an oil. Purification by flash chromatography (silica gel; 100:3 heptane:ethyl acetate) affords 12.8 grams of the title compound.
Analysis:
Calcd for $C_{22}H_{33}NO_3$: C, 73.5; H, 9.2; N, 3.9.
Found: C, 73.2; H, 9.2; N, 3.8.

Example 2B

1-Cyclohexyloxy-4-hydroxy-2,2,6,6-tetramethylpiperidine

The ester obtained in Example 2A is hydrolyzed using potassium hydroxide in aqueous methanol to give the title compound as a white solid melting at 74°–78° C.
Analysis:
Calcd for $C_{15}H_{29}NO_2$: C, 70.5; H, 11.5; N, 5.5.
Found: C, 70.3; H, 11.3; N, 5.4

Example 3A

4-Benzoyloxy-1-ethoxy-2,2,6,6-tetramethlzlpiperidine

A mixture of 28.3 grams (102 mmol) of 4-benzoyloxy-1-oxyl-2,2,6,6-tetramethylpiperidine, 5.0 grams of magnesium sulfate, 1.0 gram of 5% palladium on carbon, and 100 ml of anhydrous tetrahydrofuran is hydrogenated (50 psi, room temperature) on a Parr apparatus. Solids are removed by filtration, and ethyl iodide ( 32.1 grams, 206 mmol) is added to the crude hydroxylamine solution. A solution obtained by refluxing a suspension of 3.7 grams (154 mmol) of sodium hydride in 10 ml of dimethyl sulfoxide and 50 ml of tetrahydrofuran is then added over 30 minutes to the hydroxylamine solution. The reaction mixture is diluted with water (1 liter) and extracted with ether (2×150 ml). The combined organic layers are washed with water
(2×1000 ml), washed with saturated sodium chloride solution (500 ml), dried over anhydrous magnesium sulfate and then concentrated under reduced pressure. The crude product is purified by flash chromatography (silica gel; 9:1 hexane:ethyl acetate) and crystallized from methanol to afford 15.1 grams (48% yield) of the title compound as a white solid melting at 76°–78° C.
Analysis:
Calcd for $C_{18}H_{27}NO_3$: C, 70.8; H, 8.9; N, 4.6.
Found: C, 71.2; H, 9.1; N, 4.5.

Example 3B

1-Ethoxy,4-hydroxy-2,2,6,6-tetramethylpiperidine

The ester obtained in Example 3A is hydrolyzed using sodium hydroxide in aqueous methanol to give the title compound as a white solid melting at 86°–88° C.
Analysis:
Calcd for $C_{11}H_{23}NO_2$: C, 65.6; H, 11.5; N, 7.0.
Found: C, 66.0; H, 11.8; N, 7.0.

Example 4

4-Hydroxy-1-alpha-methylbenzyloxy-2,2,6,6-tetramethylpiperidine

A solution of 70% aqueous tert-butyl hydroperoxide (74.8 grams, 609 mmol) is added over 30 minutes to a mixture of 35.0 grams (203 mmol) of 4-hydroxy-1-oxyl-2,2,6,6-tetramethylpiperidine, 2.0 grams of molybdenum trioxide, and 200 ml of ethylbenzene which is preheated to 120° C. The reaction mixture is maintained at reflux temperature throughout the addition, and water is collected in a Dean-Stark trap. The red mixture is heated at reflux for three hours after the addition is complete in order to discharge the red color of the N-oxyl compound. Solids are removed by filtration, and the filtrate is concentrated at reduced pressure to obtain a yellow oil. Purification by flash chromatography (silica gel; 4:1 hexane:ethyl acetate) affords 30.0 grams (53% yield) of the title compound as a white solid melting at 95°–97° C.
Analysis:
Calcd for $C_{17}H_{27}NO_2$: C, 73.6; H, 9.8; N, 5.0.
Found: C, 73.4; H, 9.8; N, 5.0.

Example 5

4-Hydroxy-1-octyloxy-2,2,6,6-tetramethylpiperidine

A solution of 121.8 grams (946 mmol) of 70% aqueous tert-butyl hydroperoxide is added over a 3-hour period to a mixture of 101.5 grams (367 mmol) of 4-benzoyloxy-1-oxyl-2,2,6,6-tetramethylpiperidine, 1.3 gram of molybdenum trioxide, and 650 ml of n-octane that is preheated to 120° C. The reaction mixture is maintained at reflux temperature throughout the addition, and water is collected in a Dean-Stark trap. The reaction mixture is heated at reflux for 8.5 hours after the addition is complete in order to discharge the red color of the nitroxyl starting material. The crude reaction mixture is purified by flash chromatography (50:1 heptane: ethyl acetate ) and then hydrolyzed using potassium hydroxide in ethanol to obtain the title compound as a colorless oil.
Analysis:
Calcd for $C_{17}H_{35}NO_2$; C, 71.5; H, 12.4; N, 4.9.
Found: C, 71.4; H, 12.6; N, 4.8.

Example 6A

N-(1-Cyclohexyloxy-2,2,6,6-tetramethylpiperidin-4-yl)acetamide

A mixture of 10.0 grams (47 mmol) of N-(1-oxyl-2,2,6, 6-tetramethylpiperidin-4-yl) acetamide, 15.2 grams (118 mmol) of 70% aqueous tert-butyl hydroperoxide, 0.67 gram of molybdenum trioxide, and 75 ml of cyclohexane is heated at reflux and water is,collected in a Dean-Stark trap. The reaction mixture is then transferred to a Fischer-Porter pressure bottle and heated at 140° C. (bath temperature) for four hours to discharge the red color of the nitroxyl starting material. The reaction mixture is filtered, and the filtrate is diluted with ethyl acetate (150 ml ). The organic solution is stirred with 5% aqueous sodium sulfite (150 ml) for one hour to decompose any residual hydroperoxide, then washed with brine (150 ml), dried over anhydrous magnesium sulfate, and concentrated to obtain 12.6 grams of of white solid. Recrystallization from heptane affords 10.4 grams of the title compound as a white solid melting at 139°–144° C.
Analysis:

Calcd for $C_{17}H_{32}N_2O_2$: C, 68.9; H, 10.9; N, 9.5.
Found: C, 68.6; H, 11.3; N, 9.3.

Example 6B

4-Amino-1-cyclohexyloxy-2,2,6,6-tetramethylpiperidine

The title compound is obtained as a clear colorless oil by the hydrolysis of the acetamide prepared in Example 6A using 6N hydrochloric acid at reflux for 24 hours. The title compound is purified by Kugelrohr distillation at 140° C./1.5 mm.
Analysis:
Calcd for $C_{15}H_{30}N_2O$: C, 70.8; H, 11.9; N, 11.0.
Found: C, 68.1; H, 12.1; N, 10.5.

Example 7

N-(1-Cyclohexyloxy-2,2,6,6-tetramethylpiperidin-4-yl)-succinamic Acid

A solution of 1.0 gram (10.0 mmol) of succinic anhydride in 25 ml of acetone is added to a solution of 2.64 gram (10.0 mmol) of 4-amino-1-cyclohexyloxy-2,2,6,6tetramethylpiperidine (as prepared in Example 6B) in 10 ml of acetone. The reaction mixture is stirred for sixteen hours at room temperature and then concentrated to form a white solid. Purification by flash chromatography (silica gel; 9:1 ethyl acetate:ethanol) and recrystallization from heptane:ethyl acetate affords the title compound as a white solid melting at 136°–138 ° C.
Analysis:
Calcd for $C_{19}H_{34}N_2O_4$: C, 64.4; H, 9.7; N, 7.9.
Found: C, 64.4; H, 9.7; N, 7.8.

Example 8

4-n-Butylamino-1-cyclohexyloxy-2,2,6,6-tetramethylpiperidine

A mixture of 9.5 grams (37.5 mmol) of 1-cyclohexyloxy-2,2,6,6-tetramethylpiperidin-4-one, 13.7 grams (187 mmol) of n-butylamine, 0.4 gram of platinum oxide, and 120 ml of ethanol is hydrogenated on a Parr apparatus (50 psi, ambient temperature) till hydrogen uptake ceases. The catalyst is removed by filtration and the filtrate is evaporated to afford 10.8 grams (93% yield) of the title compound as a colorless syrup.
Analysis:
Calcd for $C_{19}H_{38}N_2O$: C, 73.5; H, 12.3; N, 9.0.
Found: C, 73.0; H, 12.6; N, 8.6.

Example 9

N-Butyl-N-(1-cyclohexyloxy-2,2,6,6-tetramethylpiperidin-4-yl)-succinamic Acid

A solution of 10.2 grams (33 mmol) of 4-n-butylamino-1-cyclohexyloxy-2,2,6,6-tetramethylpiperidine (prepared in Example 8), 3.3 grams (33 mmol) of triethylamine, and 30 ml of tetrahydrofuran is added to a solution of 3.0 grams (30 mmol) of succinic anhydride in 20 ml of tetrahydrofuran over a 5-minute period. The reaction mixture is stirred for six hours and then diluted with ethyl acetate (200 ml). The organic solution is washed with 1N hydrochloric acid (2×50 ml), washed with water (50 ml), washed with saturated sodium chloride solution (50 ml), dried over anhydrous magnesium sulfate and concentrated under reduced pressure to give an oil which crystallizes on standing. Recrystallization from heptane affords 5.6 grams (46% yield) of the title compound as a white solid melting at 110°–113° C.
Analysis:
Calcd for $C_{23}H_{42}N_2O_4$: C, 67.3; H, 10.3; N, 6.8.
Found: C, 67.4; H, 10.4; N, 6.7.

Example 10A

4-Allyloxy-1-octyloxy-2,2,6,6-tetramethylpiperidine

Sodium hydride (2.65 grams, 110 mmol) is added to a solution of 30.0 grams (105 mmol) of 4-hydroxy-1-octyloxy-2,2,6,6-tetramethylpiperidine (as prepared in Example 5) in 150 ml of tetrahydrofuran under nitrogen. The reaction mixture is heated at reflux for three hours, cooled to 35° C., and treated with 12.7 grams (110 mmol) of allyl bromide. The reaction mixture is heated at reflux for one hour, then partitioned between ethyl acetate (150 ml) and water (50 ml). The organic layer is washed with saturated sodium chloride solution (100 ml ), dried over anhydrous magnesium sulfate, and concentrated under reduced pressure. The residue is dissolved in heptane (50 ml) and passed through a pad of silica gel (eluent 5:1 heptane:ethyl acetate). The crude product is purified by flash chromatography (silica gel; 9:1 heptane:ethyl acetate) to afford 23.9 grams (70% yield) of the title compound as a colorless oil.
Analysis:
Calcd for $C_{20}H_{39}NO_2$: C, 73.8; H, 12.1; N, 4.3.
Found: C, 74.0; H, 12.7; N, 4.7.

Example 10B 3-(1-Octyloxy-2,2,6,6-tetramethylpiperidin-4-yloxy)-1-propanol

A solution of 14.9 grams ( 45.9 mmol) of 4-allyloxy-1-octyloxy-2,2,6,6-tetramethylpiperidine (prepared in Example 10A) in 20 ml of anhydrous tetrahydrofuran is added over a 10-minute period to a solution of 5.6 grams ( 45.9 mmol ) of 9-borabicyclo [3.3.1]nonane in 20 ml of tetrahydrofuran under a nitrogen atmosphere. The reaction mixture is cooled to 20° C., and a solution of 1.84 gram ( 45.9 mmol ) of sodium hydroxide in water is added over a 10-minute period. A solution of 15.3 ml of 30% aqueous hydrogen peroxide is then added over 30 minutes while the reaction mixture is cooled in an ice-water bath. The reaction mixture is diluted with ether (50 ml) and the organic layer is separated and dried over potassium carbonate. Solvent is evaporated and the residue is purified by flash chromatography (silica gel; 2:1 heptane:ethyl acetate) to afford 14.0 grams (89% yield) of the title compound is a colorless syrup.
Analysis:
Calcd for $C_{20}H_{41}NO_3$: C, 69.9; H, 12.0; N, 4.1.
Found: C, 70.1; H, 12.7; N, 4.7.

Example 11

1-(1-Octyloxy-2,2,6,6-tetramethylpiperidin-4-yloxy)-2,3-epoxypropane

A mixture of 20.0 grams (70 mmol) of 4-hydroxy-1-octyloxy-2,2,6,6-tetramethylpiperidine (prepared in Example 5), 1.68 gram (70 mmol) of sodium hydride, 2 ml of dimethyl sulfoxide, and 150 ml of tetrahydrofuran is heated at reflux for three hours. The reaction mixture is cooled to room temperature, and a solution of 6.5 grams (70 mmol) of epichlorohydrin in 50 ml of tetrahydrofuran is added over a 5-minute period. The reaction mixture is stirred sixteen hours at room temperature and then partitioned between ether and water. The aqueous layer is extracted with ether and the combined ether solutions are dried over anhydrous magnesium sulfate before concentrating to yield an oil. Purification by flash chromatography (4:1 hexane-:ethyl acetate) affords 3.9 grams (16% yield) of the title compound as a colorless oil.

Analysis:
Calcd for $C_{20}H_{39}NO_3$: C, 70.3; H, 11.5; N, 4.1.
Found: C, 70.3; H, 11.2; N, 4.8.

Example 12

3-Hydroxymethyl-3,8,8,10,10-pentamethyl-9-cyclohexyl-oxy-9-aza-1,5-dioxaspiro[5.5]undecane The title compound is prepared from by the reaction of 1-cyclohexyloxy-2,2,6,6-tetramethylpiperidin-4-one and 1,1,1-tris (hydroxymethyl)ethane in the presence of p-toluenesulfonic acid.

Example 13

1,3-Bis (1-cyclohexyloxy-2,2,6,6-tetramethylpiperidin-4-yl-oxy)-propan-2-ol

The title compound is prepared by the reaction of 1-(1-cyclohexyloxy-2,2,6,6-tetramethylpiperidin-4-yloxy)-2,3-epoxypropane (prepared in Example 11) with 4-hydroxy-1-cyclohexyloxy-2,2,6,6-tetramethylpiperidine (prepared in Example 5) and sodium hydride.

Example 14

2,3-Bis(1-octyloxy-2,2,6,6-tetramethylpiperidin-,4-yloxy)-propan-1-ol

The title compound is prepared by the reaction of 1-(1-octyloxy-2,2,6,6-tetramethylpiperidin-4-yloxy) -2,3-epoxypropane (prepared in Example 11) and 4-hydroxy-1-octyloxy-2,2,6,6-tetramethylpiperidine (prepared in Example 5) in the presence of a catalytic amount of perchloric acid.

Example 15A

N-(2,2,6,6-Tetramethylpiperidin-4-yl)acetamide

A solution of 100.0 grams (64 mmol) of 4-amino-2,2,6, 6-tetramethylpiperidine in 150 ml of toluene and a solution of 65.4 grams (64 mmol) of acetic anhydride in 175 ml of toluene are simultaneously added over a 45-minute period to a flask containing 150 ml of toluene. The reaction temperature is maintained at 25°–35° C. by using an ice water bath. The reaction mixture is stirred for 30 minutes after the addition is complete. Solids are separated by filtration, washed with ether and dissolved in 500 ml of water. This aqueous solution is added to a solution of 28 grams of sodium hydroxide in 100 ml of water. A crude solid is isolated by filtration and the filtrate is saturated with solid sodium chloride to precipitate more of the product. The solids are combined, dried and dissolved in warm isopropanol. The alcohol solution is filtered to remove salts, and the filtrate is concentrated to give an oil. The oil is crystallized from heptane to afford 111.0 grams (87% yield) of the title compound as a white solid melting at 100°–102° C.

Example 15B

N-(1-Octyloxy-2,2,6,6-tetramethylpiperidin-4-yl) acetamide

A two-phase mixture of 260 grams ( 2.02 mol ) of 70% aqueous tert-butyl hydroperoxide, 350 ml of n-octane, and 50 grams of sodium chloride is vigorously stirred. The organic phase is separated, dried over anhydrous magnesium sulfate and filtered. The filtrate is diluted with n-octane to a volumne of 580 ml. To a mixture of 100.0 grams (0.504 mol) of N-(2,2,6,6-tetramethylpiperidin-4-yl)acetamide, 1.8 gram of molybdenum trioxide, and 100 ml of n-octane preheated to 120° C. is added 300 ml of tert-butyl hydroperoxide solution over a 15-minute period. The mixture quickly turns red and water is collected in a Dean-Stark trap. The remaining tert-butyl hydroperoxide solution (280 ml) is added to-the refluxing reaction mixture over a period of 2.5 hours. The reaction mixture is heated at reflux for three hours after the addition is complete, then treated with 50.1 grams ( 0.50 mol ) of 90% tert-butyl hydroperoxide and heated at reflux for 2.5 hours to discharge the red color of the N-oxyl intermediate. Solids are removed by filtration, and the filtrate is cooled to 5° C. and stirred with a solution of 40 grams of sodium sulfite in 400 ml of water to decompose unreacted hydroperoxide. The organic layer is dried over anhydrous magnesium sulfate and concentrated to an oil. Purification by flash chromatography (1:1 heptane:ethyl acetate) affords 100.2 grams (61% yield) of the title compound as a waxy solid.

Example 15C

4-Amino-1-octyloxy-2,2,6,6-tetramethylpiperidine

A mixture of 40.0 grams (0.123 mmol) of N-(1-octyloxy-2,2,6,6-tetramethylpiperidin-4-yl)acetamide and 6N hydrochloric acid is heated at reflux for three hours. The reaction mixture is cooled and extracted with 2×150 ml). The aqueous layer is made basic and extracted with 3:1 ether:dichloromethane (3×150 ml). The three organic extracts are combined, dried over anhydrous magnesium sulfate and then concentrated to an oil. Purification by Kugelrohr distillation at 110°–120° C./0.5 mm affords 28.9 grams (83% yield) of the title compound as a pale yellow oil.

Example 16

N-(1-Octyloxy-2,2,6,6-tetramethylpiperidin-4-yl)-N'-aminooxamide

The title compound is prepared by the sequential reaction of 4-amino-1-octyloxy-2,2,6,6-tetramethylpiperidine (prepared in Example 15C) with diethyl oxalate and with ethanolamine.

Example 17

3-Hydroxymethyl-9-octyloxy-3,8,8,10,10-pentamethyl-9-aza-1,5-dioxaspiro[5.5]undecane A mixture of 11.0 grams (38.5 mmol) of 1-octyloxy-2,2, 6,6-tetramethylpiperidin-4-one, 10.2 grams (84.9 mmol) of 1,1,1-tris(hydroxymethyl)ethane, 1.4 grams of p-toluenesulfonic acid and 100 ml of toluene is heated at reflux for four hours. Water is collected in a Dean-Stark trap. Purification of the reaction mixture by flash chromatography on silica gel affords 2.1 grams (14% yield) of the title compound as a colorless syrup.

Analysis:
Calcd for $C_{22}H_{43}NO_4$: C, 68.5; H, 11.2; N, 3.6.
Found: C, 69.1; H, 11.9; N, 3.6.

Example 18A

Methyl N-(1-Cyclohexyloxy-2,2,6,6-tetramethylpiperidin-4-yl)oxamate

A mixture of 1000 grams (39.3 mmol) of 4-amino-1-cyclohexyloxy-2,2,6,6-tetramethylpiperidine, 27.8 grams (236 mmol) of dimethyl oxalate and 100 ml of toluene is heated at reflux. Methanol and toluene are removed from the reaction mixture by fractional distillation. The reaction is then filtered and the liltrate is concentrated to obtain a solid. Fractional crystallization of the solid from 9:1 isopropanol::methylene chloride followed by recrystallization from heptane affords 6.5 grams (48% yield) of the title compound as a white solid melting at 124°–126° C.

Example 18B

N-(1-Cyclohexyloxy-2,2,6,6-tetramethylpiperidin-4-yl)-N'-(2-hydroxyethyl)oxamide A mixture of 9.1 grams (26.7 mmol) of methyl N-(1-cyclohexyloxy-2,2,6,6-tetramethylpiperidin-4-yl)oxamate, 1.8 grams (29.4 mmol) of ethanolamine and 35 ml of toluene is heated at reflux for 30 minutes. Methanol is removed from the reaction mixture by fractional distillation. The reaction mixture is poured into ethyl acetate (125 ml) to afford 6.3 grams (64% yield) of the title compound as a white solid melting at 190°–192° C.
Analysis:
Calcd for $C_{19}H_{35}N_3O_4$: C, 61.8; H, 9.6; N, 11.4.
Found: C, 61.8; H, 9.8; N, 11.2.

Example 19

N-(1-Octyloxy-2,2,6,6-tetramethylpiperidin-4-yl)succinamic Acid

Following the general procedure of Example 9, 4-amino-1-octyloxy-2,2,6,6-tetramethylpiperidine is added to succinic anhydride over a 30-minute period. The reaction mixture is then stirred for two hours. The crude product is purified by flash chromatography on silica gel (9:1, ethyl acetate:methanol) followed by trituration with heptane to give the title compound in 75% yield as a white powder melting at 96°–103° C.
Analysis:
Calcd for $C_{21}H_{40}N_2O_4$: C, 65.6; H, 10.5; N, 7.3.
Found: C, 65.0; H, 10.8; N, 7.2.

Example 20

Mono-(1-cyclohexyloxy-2,2,6,6-tetramethylpiperidin-4-yl) Hydrogen Succinate

A mixture of 12.8 grams (50.0 mmol) of 1-cyclohexyloxy-4-hydroxy-2,2,6,6-tetramethylpiperidine, 5.0 grams (50.0 mmol) of succinic anhydride and 15 ml of toluene is heated at reflux for five minutes. Solvent is evaporated and the residue is dissolved in hexane. Water is added and the resulting precipitate is washed with hexane to afford 16.1 grams (90% yield) of the title compound as the monohydrate as a white solid melting at 56°–60° C.
Analysis:
Calcd for $C_{19}H_{33}NO_5 \cdot H_2O$: C, 61.1; H, 9.4; N, 3.7.
Found: C, 61.0; H, 9.0; N, 3.7.

Example 21A

4-Benzoyloxy-1-(2-cyclohexen-1-yloxy)-2,2,6,6-tetramethylpiperidine

A solution of 33.6 grams (122 mmol) of 4-benzoyloxy-1-oxyl-2,2,6,6-tetramethylpiperidine, 23.0 grams (157 mmol) of di-tert-butyl peroxide, and 70 ml of cyclohexene is heated in a Fischer-Porter pressure bottle at 138° C. for 6.5 hours. The reaction mixture is purified by flash chromatography on silica gel (200:1 heptane:ethyl acetate) to afford 35.1 grams (81% yield) of the title compound as a colorless oil.
Analysis:
Calcd for $C_{22}H_{31}NO_3$: C, 73.9; H, 8.7; N, 3.9.
Found: C, 73.7; H, 8.8; N, 3.9.

Example 21B 1,4-Bis(4-benzoyloxy-2,2,6,6-tetramethylpiperidin-1-yloxy)-2-cyclohexene A mixture of 43.6 grams (122 mmol) of the compound prepared in Example 21A, 40.5 grams (147 mmol) of 4-benzoyloxy-1-oxyl-2,2,6,6-tetramethylpiperidine, 17.8 grams (122 mmol) of di-tert-butyl peroxide and 50 ml of 1,2-dichlorobenzene is heated at 135° C. for 5.5 hours in a Fisher-Porter pressure bottle. Fresh di-tert-butyl peroxide. (8.0 grams, 55 mmol) is added and the reaction mixture is heated at 135° C. for an additional three hours. The crude reaction mixture is purified by flash chromatography on silica gel (hexane; then 100:3 heptane:ethyl acetate) to afford 4.0 grams of the title compound as a while solid melting at 140°–142° C.
Analysis:
Calcd for $C_{38}H_{52}N_2O_6$: C, 72.1; H, 8.3; N, 4.4.
Found: C, 72.0; H, 8.5; N, 4.3.

Example 21C 1,4-Bis(4-benzoyloxy-2,2,6,6-tetramethylpiperidin-1-yloxy)-cyclohexane The title compound is prepared by the catalytic hydrogenation of 1,4-bis (4-benzoyloxy-2,2,6,6-tetramethyl-piperidin-1-yloxy)-2-cyclohexane prepared in Example 21B.

Example 21D 1,4-Bis(4-hydroxy-2,2,6,6-tetramethylpiperidin-1-yloxy)cyclohexane The title compound is prepared by the basic hydrolysis (potassium hydroxide in ethanol) of the compound prepared in Example 21C.

Example 22A

Bis(4-benzoyloxy-2,2,6,6-tetramethylpiperidin-1-yloxy)octane

A mixture of 55.3 grams (0.2 mmol) of 4-benzoyloxy-2,2,6,6-tetramethylpiperid ine, 2.8 grams of molybdenum trioxide and 250 ml of n-octane is heated to 120° C. A solution of 90.2 grams (0.7 mol) of 70% aqueous tert-butyl hydroperoxide is added dropwise to the hot reaction mixture. Water is removed by azeotropic distillation and collected in a Dean-Stark trap. The reaction mixture is heated at reflux till the red color of the intermediate N-oxyl compound disappears. Solids are removed by filtration, and the filtrate is concentrated under vacuum to give an oil. Purification of the oil by flash chromatography on silica gel (100:3 heptane: ethyl acetate) affords 4-benzoyloxy-1-octyloxy-2,2,6,6-tetramethylpiperidine as a mixture of octyloxy isomers. Further elution of the chromatographic column with 50:3 heptane:ethyl acetate affords the title compound as a mixture of octanediyl isomers.

Example 22B

Bis(4-hydroxy-2,2,6,6-tetramethylpiperidin-1-yloxy)octane

The title compound is prepared by basic hydrolysis (potassium hydroxide in ethanol) of the compound prepared in Example 22A.

Example 23A 1,8-Bis(4-benzoyloxy-2,2,6,6-tetramethylpiperidin-1-yloxy)octane This reaction is carried out under a nitrogen atmosphere. Tributyltin hydride (32.1 grams, 110 mmol) is added dropwise over a three-hour interval to a solution of 66.5 grams (241 mmol) of 4-benzoyloxy-1-oxyl-2,2,6,6-tetramethylpiperidine, 20.1 grams (54.9 mmol) of 1,8-diiodooctane and 160 ml of chlorobenzene. The solution is precooled to 10° C. before addition of the tributyltin hydride begins. The reaction mixture is kept below 20° C. throughout the additions, and is then stirred at room temperature for 17 hours. The red reaction mixture is passed through a column of silica gel (heptane, then 100:3 heptane:ethyl acetate). Fractions containing the desired product are concentrated to give 26.5 grams of a crude solid. Tributyltin iodide is removed by washing a solution of the crude solid with aqueous ammonia. Final purification by flash chromatography (20:1 heptane:ethyl acetate) affords 10.6 grams of the title compound as a white solid melting at 106°–108° C. In contrast to the compound prepared in Example 22A, the title compound consists of only one octanediyl isomer.
Analysis:
Calcd for $C_{40}H_{60}N_2O_6$: C, 72.3; H, 9.1: N, 4.2.
Found: C, 72.4; H, 9.4; N, 4.0.

Example 23B 1,8-Bis(4-hydroxy-2,2,6,6-tetramethylpiperidin-1-yloxy)-octane

The title compound is prepared by basic hydrolysis (potassium hydroxide in ethanol) of the compound prepared in Example 23A.

Example 24A

Bis(4-benzoyloxy-2,2,6,6-tetramethylpiperidin-1-yloxy)-heptane

The title compound, which consists of a mixture of heptanediyl isomers, is prepared according to the procedure of Example 22A by substitution of heptane for octane.

Example 24B

Bis(4-hydroxy-2,2,6,6-tetramethylpiperidin-1-yloxy)heptane

The title compound is prepared by basic hydrolysis (potassium hydroxide in ethanol) of the compound prepared in Example 24A.

Example 25A

Bis(4-benzoyloxy-2,2,6,6-tetramethylpiperidin-1-yloxy)-cyclohexane

The title compound, which consists of a mixture of cyclohexanediyl isomers, is prepared according to the procedure of Example 22A by substituting cyclohexane for octane.

Example 25B

Bis(4-hydroxy-2,2,6,6-tetramethylpiperidin-1-yloxy)-cyclohexane

The title compound is prepared by basic hydrolysis (potassium hydroxide in ethanol) of the compound prepared in Example 25A.

Example 26A

Bis(4-acetamido-2,2,6,6-tetramethylpiperidin-1-yloxy)octane

The title compound, which consists of a mixture of octanediyl isomers, is prepared by substituting 4-acetamido-2,2,6,6-tetramethylpiperidine for 4-benzoyloxy-2,2,6,6-tetramethylpiperidine in the procedure according to Example 22A.

Example 26B

Bis(4-amino-2,2,6,6-tetramethylpiperidin-1-yloxy)octane

The title compound is prepared by the acidic hydrolysis (3N hydrochloric acid at reflux) of the compound prepared in Example 26A.

Example 27A

Mixture of Bis-and Tris-(4-benzoyloxy-2,2,6,6-tetramethyl-piperidin-1-yloxy)octadecane A mixture of 80 mmol of 4-benzoyloxy-1-oxyl-2,2,6,6-tetramethylpiperidine, 250 mmol of 90% tert-butyl hydroperoxide, 125 grams of octadecane and 5 mmol of molybdenum trioxide is heated ait 140° C. in a Fischer-Porter prerssure bottle till the red color of the N-oxyl compound is no longer visible. The reaction mixture is purified by flash chromatography.

Example 27B

Mixture of Bis- and Tris-(4-hydroxy-2,2,6,6-tetramethyl-piperidin-1-yloxy)octadecane The title mixture is prepared by the basic hydrolysis (potassium hydroxide in ethanol) of the mixture prepared in Example 27A.

Example 28A 1,4-Bis(4-benzoyloxy-2,2,6,6-tetramethylpiperidin-1-yloxy)-1,2,3,4-tetrahydronaphthalene A mixture of 80 mmol of 4-benzoyloxy-1-oxyl-2,2,6,6tetramethylpiperidine, 300 mmol of 90% tert-butyl hydroperoxide, 5 mmol of molybdenum trioxide and 80 ml of 1,2,3,4-tetrahydronaphthalene (tetralin) is heated at 135° C. in a Fischer-Porter pressure bottle till the red color of the N-oxyl starting material is no longer visible. Purification of the crude reaction mixture by flash chromatography affords the title compound.

Example 28B 1,4-Bis(4-hydroxy-2,2,6,6-tetramethylpiperidin-1-yloxy)-1,2,3,4-tetrahydronaphthalene The title compound is prepared by the basic hydrolysis (potassium hydroxide is ethanol) of the compound prepared in Example 28A.

Example 29A 1,4-Bis(4-octadecanoyloxy-2,2,6,6-tetramethyl-piperidin-1-yloxy)butane The title compound is prepared by reaction of a tetrahydrofuran solution of 1-hydroxy-4-octadecanoyloxy-2,2,6,6-tetramethylpiperidine with sodium hydride followed by reaction with 0.5 molar equivalent of 1,4-dibromobutane.

Example 29B 1,4-Bis(4-hydroxy-2,2,6,6-tetramethylpiperidin-1-yloxy)-butane

The title compound is prepared by the basic hydrolysis (potassium hydroxide in ethanol) of the compound prepared in Example 29A.

Example 30A

Bis(4-benzoyloxy-2,2,6,6-tetramethylpiperidin-1-yloxy)-methane

The reaction is carried out in a nitrogen atmosphere. Tributyltin hydride (20.0 grams, 68.7 mmol) is added dropwise over 2.75 hours to a solution, precooled to 10° C., of 40.0 grams (145 mmol ) of 4-benzoyloxy-1-oxyl-2,2,6,6-tetramethylpiperidine, 9.0 grams (33.6 mmol) of methylene iodide (diiodomethane) and 75 ml of chlorobenzene. The reaction temperature reaches 27° C. during the addition. The red mixture is stirred at room temperature for 27 hours after the addition is complete. The reaction mixture is then passed through a column of silica gel (heptane, then 100:3 heptane:ethyl acetate). Fractions containing the desired product are concentrated to give a crude solid. Tributyltin iodide is removed by washing a solution of the crude solid with aqueous ammonia. Final purification by flash chromatography on silica gel (100:3 heptane:ethyl acetate) followed by recrystallization from heptane affords 4.8 grams of the title compound as a white solid melting at 126°–127° C.
Analysis:
Calcd for $C_{33}H_{46}N_2O_6$: C, 69.9; H, 8.2; N, 4.9.
Found: C, 70.0; H, 8.2; N, 5.0.

Example 30B

Bis(4,hydroxy-2,2,6,6-tetramethylpiperidin-1-yloxy)methane

The compound is prepared by the basic hydrolysis (potassium hydroxide in ethanol) of the compound prepared in Example 30A.

Example 31A

Bis(4-acetamido-2,2,6,6-tetramethylpiperidin-1-yloxy)cyclooctane

The title compound, which consists of a mixture of cyclooctanediyl isomers, is prepared from 4-acetamido-2,2,6,6-tetramethylpiperidine and cyclooctane according to the procedure of Example 26A.

Example 31B

Bis(4-amino-2,2,6,6-tetramethylpiperidin-1-yloxy)cyclooctane

The title compound is prepared by the hydrolysis in 3N hydrochloric acid at reflux of the compound prepared in Example 31A.

Example 32A

Mixture of Bis- and Tris(4-benzoyloxy-2,2,6,6-tetramethyl-piperidin-1-yloxy)-decahydronaphthalene The title mixture is prepared according to the procedure of Example 27A by substituting decahydronaphthalene (decalin) for octadecane.

Example 32B

Mixture of Bis- and Tris (4-hydroxy-2,2,6,6-tetramethylpiperdin-1-yloxy)-decahydronaphthalene The title mixture is prepared by the basic hydrolysis (potassium hydroxide in ethanol) of the mixture prepared in Example 32A.

Example 33A

Bis(4-benzoyloxy-2,2,6,6-tetramethylpiperidin-1-yloxy)-methylcyclohexane

The title compound, which consists of a mixture of methylcyclohexanediyl isomers, is prepared from 4-benzoyl-oxy-1-oxyl-2,2,6,6-tetramethylpiperidine and methylcyclohexane according to the procedure of Example 22A.

Example 33B

Bis(4-hydroxy-2,2,6,6-tetramethylpiperidin-1-yloxy)methylcyclohexane

The title compound is prepared by the basic hydrolysis (potassium hydroxide in ethanol) of the compound prepared in Example 34A.

Example 34A 2,2-Bis(4-benzoyloxy-2,2,6,6-tetramethylpiperidin-1-yl-oxy)-propane.

The title compound is prepared from 4-benzoyloxy-1-oxyl-2,2,6,6-tetramethylpiperidine and 2,2-dibromopropane according to the procedure of Example 30A.

Example 34B 2,2,-Bis(4-hydroxy-2,2,6,6-tetramethylpiperidin-1-yloxy)propane

The title compound is prepared by the basic hydrolysis (potassium hydroxide in ethanol) of the compound prepared in Example 34A.

Example 35

1,3-Bis(1-octyloxy-2,2,6,6-tetrmethylpiperidin-4-yl-oxy)propan-2-ol

Sodium hydride (0.7 g. 5.9 mmol) is added to a solution of 17.0 g (59.5 mmol) of 1-(1-octyloxy-2,2,6,6-tetramethylpiperidin-4-yloxy)-2,3-epoxypropane (prepared in Example 11) in 75 ml of dioxane. The reaction mixture is heated at reflux for 10 minutes and then cooled to 60° C., whereupon a solution of 10.0 g (29.3 mmol) of 4-hydroxy-1-octyloxy-2,2,6,6-tetramethylpiperidine (prepared in Example 5) in 25 ml of dioxane is rapidly added. The reaction mixture is heated at reflux for 4 hours, treated with an additional 0.6 g of sodium hydride, and heated at reflux for 7 hours. The reaction mixture is diluted with diethyl ether (500 ml), and the organic solution is washed with 1N hydrochloric acid (2×100 ml) and saturated sodium bicarbonate solution, dried over magnesium sulfate, and concentrated to an oil. Purification by flash chromatography on silica gel (9:1 heptane: ethyl acetate ) affords 8.4 g (46% yield) of the title compound, a colorless oil.

Anal. Calcd. for $C_{37}H_{74}N_2O_5$: C 70.9; H 11.9; N 4.5.
Found: C 71.1; H 12.3; N 4.7.

Example 36

The following data show the advantages of incorporating the instant compounds with reactable functional groups into coatings over the current state of the art. These advantages included improved compatibility with the coating, improved thermal permanence, and greatly reduced extractability and migrating ability.

A model polyester urethane is formulated as shown in Table 1. To this material is added 2% (by weight on total resin solids) of various hindered amines. 5 g of each polymer formulated coating solution are placed into glass vials.

TABLE 1

| | Parts by Weight |
|---|---|
| Desmophen 670-80 (Polyester polyol from Mobay) | 41.3 |
| Desmodur N-75 (polyisocyanate from Mobay) | 23.1 |
| Xylene | 17.8 |
| PM Acetate | 17.8 |
| | 100.0 |

Example 36A

Improved Compatibility

The stabilized polyester urethane samples are allowed to cure in the vials for 20 hours and are visually examined. The results are listed below.

| Additive | Observation |
|---|---|
| Unstabilized | Clear, transparent |
| 2% Compound of Example 5 | Clear, transparent |

Similarly, drawdowns of these coatings are made over glass plates and the coatings are cured by baking in a 170° F. (77° C.) oven for 1 hour. The coatings containing 2% by weight of the compound of Example 5 are clear and transparent.

Example 36B

Reduced Extractability

The stabilized coatings as described in Table 1 are drawn down onto glass plates using a 6 mil drawdown bar. The samples are baked for 1 hour at 170° F. (77° C.) and the clearcoat is removed from the glass plate using a razor blade.

The clearcoat samples are treated with refluxing toluene (110° C.) for 1 hour. The samples are filtered and the supernatant liquid is analyzed using a gas chromatograph. The concentration of the additive extracted is calculated using the external standard technique. The results are as follows:

| Additive | Percent of Initially Added Additive Extracted* |
|---|---|
| Compound of A** | 70 |
| Compound of Example 5 | 7.5 |
| Compound of Example 10B | 0 |

*Non-reactive additives are much more readily extracted than the instant compounds.
**Compound A is propionate ester of compound of Example 5.

Example 36C

Polycarbonate polymers are known to be degraded when treated with amines. The clearcoat described in Table 1 is spray applied onto a polycarbonate (Xenoy) substrate to a thickness of 1.5 mils. The coatings are baked for 30 minutes at 170° F. (77° C.) and then allowed to stand at ambient temperature for 3 days. The coated panels are placed inside 8 oz. (237 ml) glass jars containing 2 ml of water. The capped jars are placed in a 130° F. (54° C.) oven for 14 days. The samples are removed from the jar, blotted dry and then tested for adhesion using the crosshatched adhesion test (ASTM Method D-3359-83). The results are as follows:

| Additive | Adhesion Loss |
|---|---|
| Compound of Example 5 | 0% |

The instant compound does not adversely affect the adhesion between the coating and the plastic substrate.

Example 37

Stabilization Of High Solids Thermoset Acrylic Resin Enamel

A thermoset acrylic enamel based on a binder of 70% by weight of 2-hydroxyethyl acrylate, butyl acrylate, methyl methacrylate, styrene and acrylic acid and of 30% by weight of a melamine resin in the presence of an acid catalyst, p-toluenesulfonic acid, dinonylnaphthalene disulfonic acid or dodecylbenzenesulfonic acid, is formulated to include 2% by weight based on the resin solids of a benzotriazole ultraviolet absorber and an effective stabilizing amount of the test hindered amine light stabilizer.

Commercially available epoxy primed 4"×12" (10.16 cm×30.48 cm) panels (Uniprime from Advanced Coatings Technology) are spray coated with a silver metallic basecoat to a thickness of about 0.8 mil (0.023 mm) and air dried for 3 minutes. The stabilized thermoset acrylic resin enamel is then sprayed onto the basecoated panel to a thickness of about 1.7 mil (0.049 mm). After 15 minutes air-drying, the coated sheets are baked for 30 minutes at 250° F. (121° C.).

After storage for 1 week in an air-conditioned room, these coated panels are weathered in a QUV apparatus according to ASTM G-53/77 using FS-40 bulbs. In this test, the samples are subjected to weathering in repeated cycles for 4 hours in a humid environment at 50 degrees C. and then for 8 hours under UV light at 70 degrees C. The 20 degree gloss is measured at 300 hour intervals.

| | 20 Degree Gloss | | | | |
|---|---|---|---|---|---|
| | Hours QUV Exposure (FS-40) | | | | |
| Additive **(% by weight) | 0 | 899 | 1202 | 1852 | 2120 |
| Control | 90 | 71 | 29* | | |
| 2% UV Absorber A plus 1% HALS A | 94 | 99 | 95 | 35* | |
| 2% UV Absorber B plus 1% Compound of Example 5 | 97 | 98 | 98 | 93 | 95 |
| 2% UV Absorber B plus 1% Compound of Example 10B | 97 | 98 | 98 | 94 | 97 |
| 2% UV Absorber B plus 1% Compound of Example 11 | 91 | 97 | 99 | 84 | 71 |
| 2% UV Absorber B plus 1% Compound I | 97 | 98 | 99 | 74 | 31* |
| 2% UV Absorber B plus 1% Compound II | 96 | 99 | 97 | 91 | 85 |
| 2% UV Absorber D plus 1% Compound of Example 5 | 99 | 97 | 99 | 94 | 98 |

*indicates cracking
**UV Absorber A is 2-[2-hydroxy-3,5-di(alpha,alpha-dimethyl-benzyl)phenyl]-2H-benzotriazole.
UV Absorber B is 2-[2-hydroxy-3-tert-butyl-5(2-octyloxy-carbonyl)ethylphenyl]-2H-benzotriazole.
UV Absorber D is 2-[2-hydroxy-3-tert-butyl-5-(3-hydroxy-propyl)phenyl]-2H-benzotriazole.
HALS A is 8-acetyl-7-dodecyl-7,7,9,9-tetramethyl-(1,3,8-triazaspiro[4.5]decane-2,4-dione.
Compound I is 4-n-butylamino-1-methoxy-2,2,6,6-tetra-methylpiperidine.
Compound II is dodecyl 3-[N-(1-octyloxy-2,2,6,6-tetra-methylpiperidin-4-yl)-N-hydroxyamino]propionate.

Example 38

Light Stabilization of Polypropylene

This example illustrates the light stabilizing effectiveness of instant stabilizers.

Polypropylene powder (Himont Profax 6501) stabilized with 0.2% by weight of n-octadecyl 3,5-di-tert-butyl-4-hydroxyhydrocinnamate is thoroughly blended with the indicated amount of additive. The blended materials are then milled on a two-roll mill at 182° C. for five minutes, after which time the stabilized polypropylene is sheeted from the mill and allowed to cool. The milled polypropylene is then cut into pieces and compression molded on a hydraulic press at 250° C. and 175 psi ($1.2 \times 10^6$ Pa) into 5 mil (0.127 mm) films. The sample is exposed in a fluorescent sunlight/black light chamber until failure. Failure is taken as the hours required to reach 0.5 carbonyl absorbance by infrared spectroscopy on the exposed films.

The time to failure for a polypropylene composition containing an instant compound as stabilizer is far longer than the time to failure for polypropylene having no such stabilizer present.

Example 39

A commercial white acrylic polyurethane refinish enamel is stabilized with 2% UV Absorber and 2% of a hindered amine derivative (% by weight based on total resin solids). This material is spray applied to a thickness of 2.4–2.6 mil onto steel panels primed with a commercial epoxy-amine primer. After storage for 1 month in an air-conditioned room, the coated panels are weathered in a Xenon Arc Weatherometer. 20 degree gloss values are reported below.

| 20 Degree Gloss after Xenon exposure | | | |
|---|---|---|---|
| Compound | 0 | 1845 | 3085 Hours |
| Unstabilized | 85 | 52 | 30 |
| 2% UV Absorber C plus 1% Compound of Example 5 | 85 | 79 | 68 |
| 2% UV Absorber D plus 1% Compound of Example 5 | 86 | 82 | 72 |

UV Absorber C is 2-[2-hydroxy-3-tert-butyl-5(2-(omega-hydroxy-octa-(ethyleneoxy)carbonyl)-ethylphenyl[-2-H-benzotriazole.
UV Absorber D is 2-[2-hydroxy-3-tert-butyl-5-(3-hydroxypropyl) phenyl]-2H-benzotriazole.

Example 40

Stabilization of a Two-component Polyester Urethane Clearcoat

The following two-component clearcoat formulation is prepared:

| | Parts by Weight | Solids | meq |
|---|---|---|---|
| Desmophen 670-8- (polyester polyol from Mobay) | 61.9 | 49.5 | 123.8 |
| Desmodur N-75 (hexamethylene diisocyanate biuret from Mobay) | 34.7 | 26.0 | 136.1 |
| Xylene | 21.4 | | |
| PM Acetate (propylene glycol methyl ether acetate) | 26.7 | | |
| Dibasic Ester Solvent (dimethyl adipate/dimethyl glutarate/dimethyl succinate mixture) | 5.3 | | |
| 1% Catalyst T-12 Solution (dibutyl tin dilaurate) | 1.1 | (.015% on resin solids) | |

The formulations are stabilized with the indicated materials in the indicated concentrations (by weight on total resin solids). They are spray applied to a film thickness of 1.7–1.8 mils over a 0.6 mil thick silver metallic waterborne basecoat, which has been spray applied to 4 inch×12 inch electrocoat-primed cold rolled steel panels (available from Advanced Coating Technology, Inc. ) and prebaked for 5 minutes at 180° F. (82° C.). They are baked at 180° F. (82° C.) for 30 minutes.

The panels are exposed in a QUV weatherometer according to ASTM G-53/77 using FS-40 bulbs. 20 degree gloss values are determined as tabulated below:

| Compound (% by weight) | 20 Deg Gloss after Hours QUV Exposure | | | | | |
|---|---|---|---|---|---|---|
| | 0 | 1811 | 2139 | 2530 | 2898 | 3083 |
| Unstabilized | 93 | 51 | 36* | | | |
| 2% Compound of Example 5 | 93 | 61 | 44 | 36 | 42* | |
| 2.0% Compound of Example 10B | 93 | 67 | 39 | 33 | 40* | |
| 2.0% UV Absorber D | 94 | 58 | 51 | 43* | | |
| 2.0% UV Absorber D + 2.0% Compound of Example 5 | 94 | 73 | 53 | 49 | 58 | 60* |
| 2.0% UV Absorber D + 2.0% Compound of Example 10B | 94 | 58 | 48 | 47 | 55 | 67* |

*Indicates cracking

Example 5 is 1-octyloxy-4-hydroxy-2,2,6,6-tetramethylpiperidine.

Example 10B is 4-(3-hydroxyprop-1-oxy)-1-octyloxy-2,2,6,6-tetramethylpiperidine.

UV Absorber D is 2-[2-hydroxy-3-tert-butyl-5-(3-hydroxypropyl) phenyl]-2H-benzotriazole.

What is claimed is:

1. A 1-hydrocarbyloxy substituted hindered amine compound having the formula V,

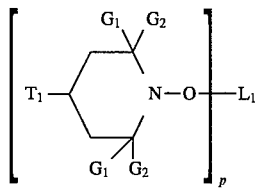

where p is 2 to 10, $L_1$ is a p-valent radical of an alkane or alkene of 1 to 18 carbon atoms, a p-valent radical of a cycloalkane or cycloalkene of 5 to 12 carbon atoms, a p-valent radical of a saturated or unsaturated bicyclic or tricyclic hydrocarbon of 7 to 12 carbon atoms or a p-valent radical of an aryl, alkyl substituted aryl or aralkyl hydrocarbon of 6 to 15 carbon atoms, with the proviso that the N-O groups are not necessarily attached to the same carbon atom in $L_1$, $T_1$ is —OH, —$NHR_2$, —NCO, —O—glycidyl or $Si(OR_1)_3$, $G_1$ and $G_2$ are independently alkyl of 1 to 4 carbon atoms, or $G_1$ and $G_2$ together are pentamethylene, where $R_1$ is hydrogen or alkyl of 1 to 12 carbon atoms, where $R_2$ is hydrogen, alkyl of 1 to 12 carbon atoms, or

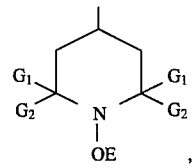

and where

E is alkyl of 1 to 18 carbon atoms, cycloalkyl of 5 to 12 carbon atoms, alkenyl of 2 to 18 carbon atoms, propargyl, cycloalkenyl of 5 to 12 carbon atoms, aralkyl of 7 to 15 carbon atoms, a radical of a saturated or unsaturated bicyclic or tricyclic hydrocarbon of 7 to 12 carbon atoms or aryl of 6 to 10 carbon atoms or said aryl substituted by alkyl.

2. A compound according to claim 1 where $G_1$ and $G_2$ are each methyl.

3. A compound according to claim 1 wherein E is alkyl of 1 to 18 carbon atoms, alkenyl of 2 to 3 carbon atoms, propargyl or cyclohexyl.

4. A compound according to claim 3 wherein E is methyl, heptyl, octyl, nonyl or cyclohexyl.

5. A compound according to claim 1 wherein $L_1$ is an n-valent radical of n-octane, n-heptane or cyclohexane.

6. The compound according to claim 1 wherein $T_1$ is —OH or —$NH_2$.

* * * * *